United States Patent
Kageyama et al.

(10) Patent No.: US 10,611,726 B2
(45) Date of Patent: Apr. 7, 2020

(54) METHOD FOR PRODUCING POLYTHIOL COMPOUND, METHOD FOR PRODUCING CURABLE COMPOSITION, AND METHOD FOR PRODUCING CURED PRODUCT

(71) Applicant: HOYA LENS THAILAND LTD., Prachatipat, Thanyaburi, Pathumthani (TH)

(72) Inventors: Yukio Kageyama, Tokyo (JP); Masahisa Kousaka, Tokyo (JP); Tomofumi Ohnishi, Tokyo (JP)

(73) Assignee: HOYA LENS THAILAND LTD., Pathumthani (TH)

( * ) Notice: Subject to any disclaimer, the term of this patent is extended or adjusted under 35 U.S.C. 154(b) by 0 days.

(21) Appl. No.: 16/015,620

(22) Filed: Jun. 22, 2018

(65) Prior Publication Data

US 2018/0297943 A1 Oct. 18, 2018

Related U.S. Application Data

(63) Continuation of application No. PCT/JP2017/028731, filed on Aug. 8, 2017.

(30) Foreign Application Priority Data

Aug. 8, 2016 (JP) .................................. 2016-155875

(51) Int. Cl.
  *C07C 319/14* (2006.01)
  *C07C 319/22* (2006.01)
  (Continued)

(52) U.S. Cl.
  CPC .......... *C07C 319/14* (2013.01); *C07C 319/20* (2013.01); *C07C 319/22* (2013.01);
  (Continued)

(58) Field of Classification Search
  CPC ... C07C 319/14; C07C 319/20; C07C 321/14; C07C 319/22; C08G 18/3876;
  (Continued)

(56) References Cited

U.S. PATENT DOCUMENTS

| | | | | |
|---|---|---|---|---|
| 5,608,115 A | * | 3/1997 | Okazaki ................ | C07C 321/14 568/61 |
| 2009/0264613 A1 | * | 10/2009 | Kuma ................... | C07C 319/14 528/60 |
| 2015/0126781 A1 | * | 5/2015 | Kawaguchi ........... | G02B 1/041 568/57 |

FOREIGN PATENT DOCUMENTS

| | | |
|---|---|---|
| CN | 104321306 A | 1/2015 |
| EP | 2845848 A1 | 3/2015 |

(Continued)

OTHER PUBLICATIONS

Oct. 3, 2017 Search Report issued in International Patent Application No. PCT/JP2017/028731.

(Continued)

*Primary Examiner* — Rabon A Sergent
(74) *Attorney, Agent, or Firm* — Oliff PLC

(57) ABSTRACT

Provided is a method for producing a polythiol compound, including obtaining one or more polythiol compounds selected from the group consisting of a polythiol compound represented by Formula (3), a polythiol compound represented by Formula (4), and a polythiol compound represented by Formula (5) through steps including: reacting 2-mercaptoethanol with an epihalohydrin in an amount of 1.00 equivalent or more and 1.25 equivalent or less with respect to the 2-mercaptoethanol to obtain a polyol compound represented by Formula (1); and reacting the polyol compound represented by Formula (1) with an alkali metal sulfide in an amount of 1.04 equivalent or more and 1.25 equivalent or less with respect to the 2-mercaptoethanol to obtain a polyol compound represented by Formula (2).

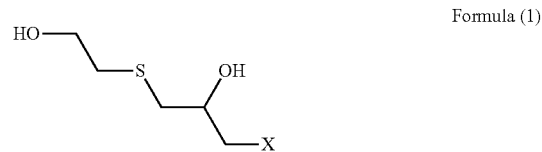

Formula (1)

[in Formula (1), X represents a halogen atom]

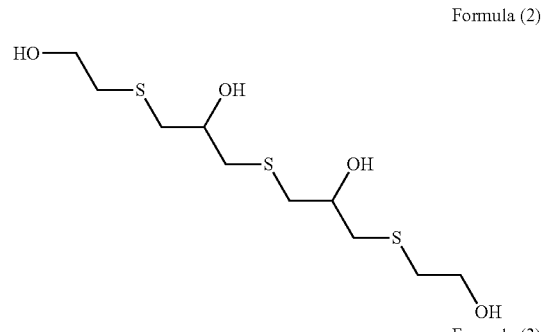

Formula (2)

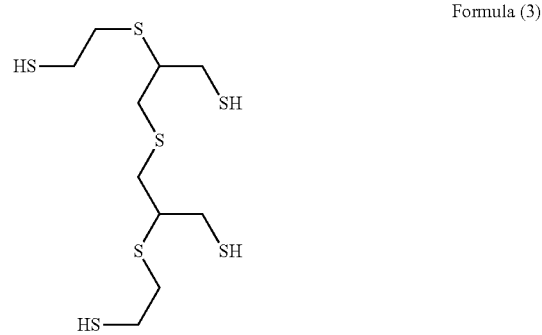

Formula (3)

(Continued)

-continued

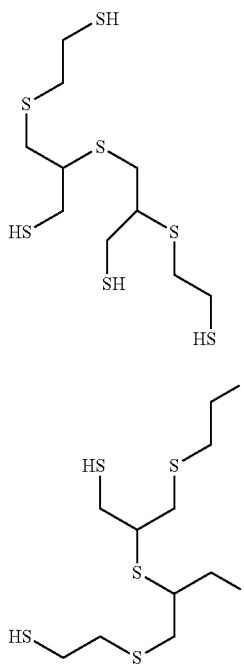

Formula (4)

Formula (5)

6 Claims, No Drawings

(51) Int. Cl.
*C07C 321/14* (2006.01)
*G02B 1/04* (2006.01)
*G02C 7/00* (2006.01)
*G02B 3/00* (2006.01)
*C08G 18/38* (2006.01)
*C07C 319/20* (2006.01)
*C08G 18/76* (2006.01)

(52) U.S. Cl.
CPC ............ *C07C 321/14* (2013.01); *C08G 18/38* (2013.01); *C08G 18/3876* (2013.01); *C08G 18/7642* (2013.01); *G02B 1/04* (2013.01); *G02B 1/041* (2013.01); *G02B 3/00* (2013.01); *G02C 7/00* (2013.01)

(58) Field of Classification Search
CPC .... C08G 18/7642; C08G 18/38; G02B 1/041; G02B 1/04; G02B 3/00; G02C 7/00
See application file for complete search history.

(56) References Cited

FOREIGN PATENT DOCUMENTS

| | | | |
|---|---|---|---|
| JP | H07-252207 | A | 10/1995 |
| JP | 2004-2340 | A | 1/2004 |
| JP | 2015-520765 | A | 7/2015 |
| WO | 2014/027428 | A1 | 2/2014 |
| WO | 2016/052121 | A1 | 4/2016 |

OTHER PUBLICATIONS

Feb. 12, 2019 International Preliminary Report on Patentability in International Patent Application PCT/ JP2017/028731.
Mar. 26, 2019 Office Action issued in Japanese Patent Application No. 2016-155875.
Jul. 29, 2019 Office Action issued in Chinese Patent Application No. 201780005129.3.
Jun. 26, 2019 Extended European Search Report issued in European Patent Application No. 17839461.5.

* cited by examiner

METHOD FOR PRODUCING POLYTHIOL COMPOUND, METHOD FOR PRODUCING CURABLE COMPOSITION, AND METHOD FOR PRODUCING CURED PRODUCT

CROSS-REFERENCE OF RELATED APPLICATIONS

This application is a Continuation of PCT International Application No. PCT/JP2017/028731 filed on Aug. 8, 2017, which was published under PCT Article 21(2) in Japanese and claims priority under 35 U.S.C § 119(a) to Japanese Patent Application No. 2016-155875 filed on Aug. 8, 2016. The above applications are hereby expressly incorporated by reference, in their entirety, into the present application.

TECHNICAL FIELD

One aspect of the present disclosure relates to a method for producing a polythiol compound, a method for producing a curable composition, and a method for producing a cured product.

BACKGROUND ART

Polythiol compounds have been used as synthetic raw materials for obtaining various resins (see Japanese Patent Application Laid-open No. H07-252207 (the entire disclosure of which is hereby specifically incorporated by reference)). For example, a polythiourethane resin can be synthesized by a curing reaction of a polythiol compound and a polyiso(thio)cyanate compound. The polythiourethane resin thus obtained is useful as a material for various optical components such as spectacle lenses.

SUMMARY

A high refractive index exemplifies a physical property desired for the polythiourethane resins. For example, taking a spectacle lens as an example, the higher the refractive index of the polythiourethane resin constituting the lens base material of the spectacle lens, the thinner the spectacle lens can be produced. Further, a high refractive index is desired not only for the spectacle lenses but also for various optical members because the optical member can be reduced in thickness, and therefore contribution can be made to size reduction and weight reduction of the product provided with the optical member.

According to one aspect of the present disclosure, there is provided means for improving the refractive index of a polythiourethane resin obtained by a curing reaction between a polythiol compound and a polyiso(thio)cyanate compound.

One aspect of the present disclosure relates to a method for producing a polythiol compound, including:

reacting 2-mercaptoethanol with an epihalohydrin in an amount of 1.00 equivalent or more and 1.25 equivalent or less with respect to the 2-mercaptoethanol to obtain a polyol compound represented by Formula (1) (hereinafter referred to as "Step 1");

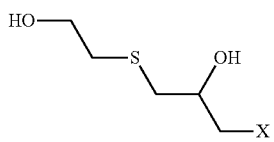

Formula (1)

[in Formula (1), X represents a halogen atom]

reacting the polyol compound represented by Formula (1) with an alkali metal sulfide in an amount of 1.04 equivalent or more and 1.25 equivalent or less with respect to the 2-mercaptoethanol to obtain a polyol compound represented by Formula (2) (hereinafter referred to as "Step 2");

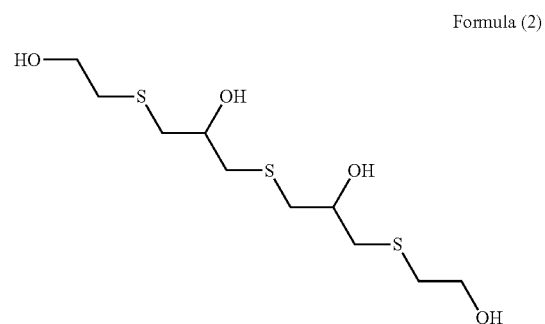 [SMILES: OCCSCC(O)CSCC(O)CSCCO]

Formula (2)

reacting the polyol compound represented by Formula (2) with thiourea in the presence of an acid to obtain an isothiuronium salt (hereinafter referred to as "Step 3");

hydrolyzing the isothiuronium salt in the presence of a base to obtain a polythiol salt (hereinafter referred to as "Step 4"); and converting the polythiol salt into a polythiol with an acid to obtain one or more polythiol compounds selected from the group consisting of a polythiol compound represented by Formula (3), a polythiol compound represented by Formula (4), and a polythiol compound represented by Formula (5) (hereinafter referred to as "Step 5").

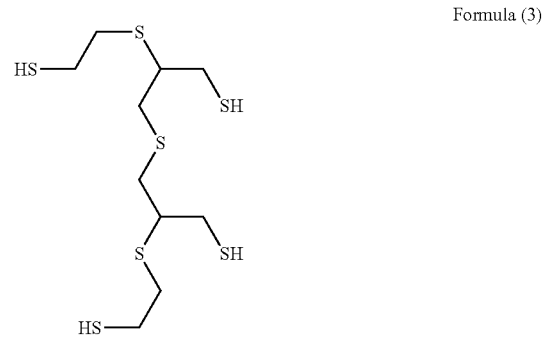

Formula (3)

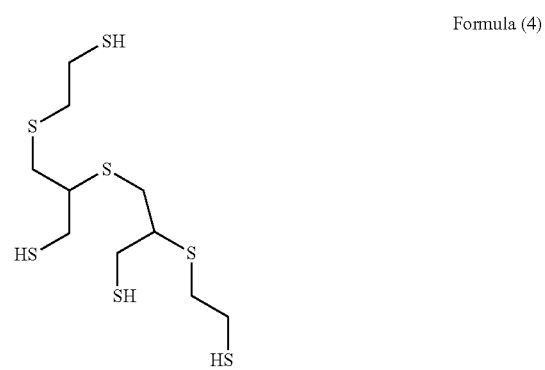

Formula (4)

Formula (5)

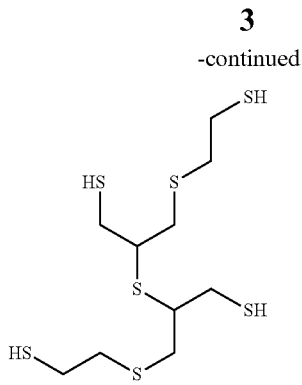

The inventors of the present disclosure have conducted an intensive study to find means for improving the refractive index of a polythiourethane resin obtained by the curing reaction between a polythiol compound and a polyiso(thio) cyanate compound. The resultant new finding, which has not been heretofore known, is that the amount of the epihalohydrin and the alkali metal sulfide charged in the process of producing the polythiol compound, which is a starting material for the synthesis of the polythiourethane resin, affects the refractive index of the polythiourethane resin obtained by the curing reaction between the polythiol compound and the polyiso(thio)cyanate compound. Subsequent intensive study based on this finding resulted in completion of a method for producing a polythiol compound according to the abovementioned one aspect of the present disclosure.

According to one aspect of the present disclosure, it is possible to improve the refractive index of a polythiourethane resin obtained by the curing reaction between a polythiol compound and a polyiso(thio)cyanate compound.

[Method for Producing Polythiol Compound]

A method for producing a polythiol compound according to one aspect of the present disclosure includes Step 1 to Step 5 mentioned hereinabove. Hereinafter, these steps will be described in greater detail.

(Step 1)

In Step 1, a polyol compound represented by the following Formula (1) can be obtained by reacting 2-mercaptoethanol with an epihalohydrin.

Formula (1)

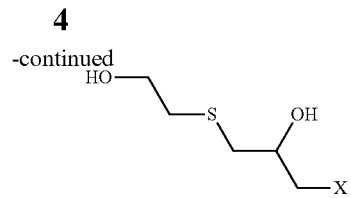

That is, in Step 1, the polyol compound represented by Formula (1) can be obtained according to the following Reaction Scheme Example 1.

Reaction Scheme Example 1

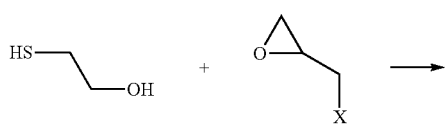

-continued

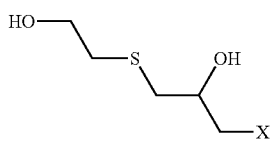

In the epihalohydrin and in Formula (1), X represents a halogen atom. For example, by using epichlorohydrin (X=chlorine atom) as the epihalohydrin in Step 1, a polyol compound in which X in Formula (1) is a chlorine atom can be obtained. Further, by using epibromohydrin (X=bromine atom) as the epihalohydrin in Step 1, a polyol compound in which X in Formula (1) is a bromine atom can be obtained. In the epihalohydrin and in Formula (1), X is, for example, a fluorine atom, a chlorine atom, a bromine atom, an iodine atom or the like, may be a chlorine atom and a bromine atom, or may be a chlorine atom. Step 1 is carried out by reacting 2-mercaptoethanol with an epihalohydrin in an amount of 1.00 equivalent or more and 1.25 equivalent or less with respect to the 2-mercaptoethanol. The equivalent of the epihalohydrin referred to herein is a charge equivalent calculated from the charged amount of 2-mercaptoethanol and the charged amount of the epihalohydrin. The inventors of the present disclosure presume that the addition of the epihalohydrin to the reaction system in the abovementioned charged amount in Step 1 and the addition of an alkali metal sulfide to the reaction system in the below-described charged amount in the below-described Step 2 contribute to the improvement of the refractive index of the polythiourethane resin obtained by the curing reaction of the produced polythiol compound with a polyiso(thio)cyanate compound. This effect was newly found as a result of the intensive investigation conducted by the inventors of the present disclosure. The charge equivalent of the epihalohydrin in Step 1 may be 1.20 equivalent or less, may be 1.15 equivalent or less, may be 1.10 equivalent or less, or may be 1.05 equivalent or less with respect to the 2-mercaptoethanol. Further, the charge equivalent of epihalohydrin in Step 1 may be, for example, 1.02 equivalent or more, 1.03 equivalent or more or 1.04 equivalent or more with respect to the 2-mercaptoethanol, but may also be 1.00 equivalent or more.

The reaction of 2-mercaptoethanol and the epihalohydrin in Step 1 may be carried out in the presence of a catalyst. As the catalyst, various known catalysts can be used, and it is possible to use a tertiary amine. Tertiary amines may be tertiary alkyl amines. Specific examples of tertiary amines include trimethylamine, triethylamine, tripropylamine, tributylamine, N,N-dimethylcyclohexylamine, N,N-dicyclohexylmethylamine, and the like.

The reaction temperature in Step 1 and the reaction temperature in Step 2 described hereinbelow can be, for example, about 0° C. to 60° C. The reaction time in Step 1 can be, for example, about 0.5 h to 10 h. In the present disclosure and the present description, the "reaction temperature" is the liquid temperature of a reaction solution and is also referred to as "internal temperature".

In one aspect, Step 1 can be carried out, for example, in the following manner. First, a solution including 2-mercaptoethanol is prepared. Here, it is possible to mix a catalyst, and it is possible to mix a tertiary amine. If necessary, a solvent (for example, an alcohol) may be added. Then, an epihalohydrin is added to the solution. The epihalohydrin may be added dropwise to the solution. The dropping time can be, for example, about 0.1 h to 5 h, but is not particularly limited. During the dropwise addition, the solution may be stirred as necessary. The charge equivalent of the epihalohydrin is as described above. The tertiary amine can be used in an amount of, for example, about 0.005 mol to 0.1 mol with respect to 1.0 mol of the epihalohydrin. After adding the epihalohydrin, the above solution may be aged for about 0.5 h to 10 h, if necessary. During aging, the solution may be allowed to stand or may be stirred. In Step 1, one or more tertiary amines can be used as the tertiary amine. When two or more tertiary amines are used, the amount of tertiary amine is assumed to be the total content of the two or more tertiary amines. In the present disclosure and the present description, unless otherwise specified, components that can take different structures may be used singly or in combination of two or more thereof. When two or more components are used, the content means the total content of the two or more components.

(Step 2)

Step 2 is a step of reacting the polyol compound obtained in Step 1 and represented by Formula (1) with an alkali metal sulfide to obtain a polyol compound represented by Formula (2).

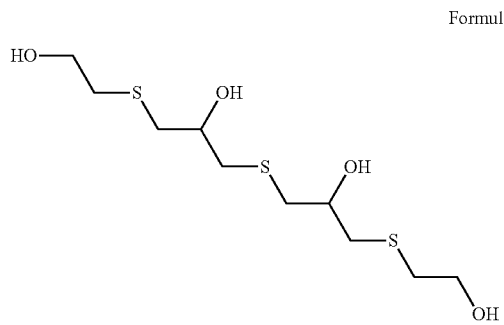

Formula (2)

The reaction between the polyol compound represented by Formula (1) and the alkali metal sulfide in Step 2 is carried out by reacting the polyol compound represented by Formula (1) with an alkali metal sulfide in an amount of 1.04 equivalent or more and 1.25 equivalent or less with respect to the 2-mercaptoethanol used in Step 1. The equivalent amount of the alkali metal sulfide referred to herein is a charge equivalent calculated from the charged amount of 2-mercaptoethanol in Step 1 and the charged amount of the alkali metal sulfide in Step 2. The alkali metal sulfide may be in the form of a hydrate. An equivalent for a hydrate refers to an equivalent including water of hydration. The inventors of the present disclosure presume that the addition of the epihalohydrin to the reaction system in the abovementioned charged amount in Step 1 and the addition of the alkali metal sulfide to the reaction system in the abovementioned charged amount in Step 2 contribute to the improvement of the refractive index of the polythiourethane resin obtained by the curing reaction of the produced polythiol compound with a polyiso(thio)cyanate compound. The charge equivalent of the alkali metal sulfide in Step 2 may be 1.20 equivalent or less, may be 1.15 equivalent or less, or may be 1.10 equivalent or less with respect to the 2-mercaptoethanol added to the reaction system in Step 1. Further, the charge equivalent of the alkali metal sulfide in Step 2 is 1.04 equivalent or more, or may be 1.05 equivalent or more with respect to the 2-mercaptoethanol added to the reaction system in Step 1.

For example, taking, as an example, the case of using sodium sulfide as an alkali metal sulfide, in Step 2, the polyol compound represented by Formula (2) can be obtained according to the following Reaction Scheme Example 2. The numerical values described in the following reaction scheme examples are on a molar basis.

Reaction Scheme Example 2

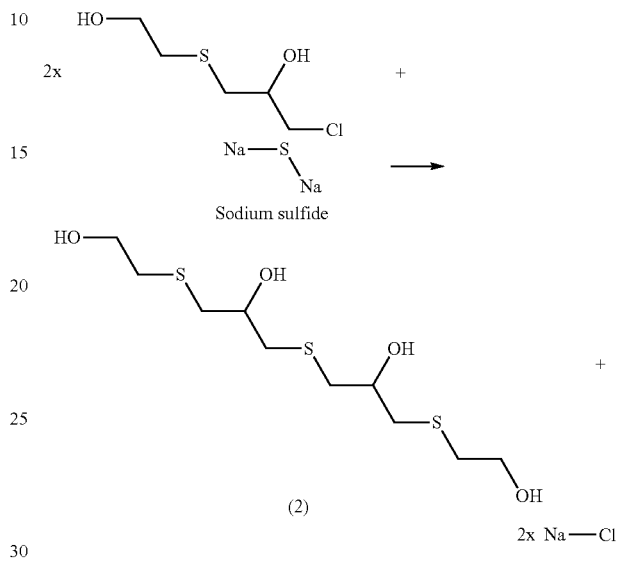

After the reaction of Step 1, the reaction solution including the target substance obtained by the reaction may be used as it is in Step 2, but the reaction solution after the reaction in Step 1 may be also purified by a known method to isolate the target substance or increase the concentration thereof and then used in the next step. Alternatively, the reaction solution after the reaction in Step 1 can be diluted with a solvent (for example, toluene and the like) and then used in the next step. The above considerations are also applicable to stages after various below-described reactions.

The abovementioned Reaction Scheme Example 2 relates to an example in which the alkali metal atom contained in the alkali metal sulfide is a sodium atom. However, the alkali metal atom contained in the alkali metal sulfide may be another alkali metal atom such as a lithium atom and a potassium atom. The alkali metal sulfide may be used as it is for the reaction of Step 2, or may be used in the form of a solution such as an aqueous solution. In one aspect, the solution of the alkali metal sulfide can be added dropwise to a reaction solution including the polyol compound represented by Formula (1). The dropping time can be, for example, about 0.1 h to 5 h, but is not particularly limited. During the dropwise addition, the reaction solution may be stirred as necessary. Such a reaction solution may be aged for about 0.5 h to 10 h as necessary after the addition of the alkali metal sulfide. During aging, the reaction solution may be left to stand or may be stirred.

(Step 3)

Step 3 is a step of reacting the polyol compound obtained in Step 2 and represented by Formula (2) with thiourea in the presence of an acid to obtain an isothiuronium salt. The "isothiuronium salt" is a quaternary salt of isothiourea. Taking, as an example, the case of using hydrochloric acid as an acid, for example, when a polyol compound represented by Formula (2) is reacted with thiourea in the presence of an acid, the isothiuronium salt shown in the following Reaction Scheme Example 3 can be obtained. In Reaction Scheme Example 3, the isothiuronium salt having the skeleton of the polythiol compound (3) is shown, but in this reaction, it is possible to obtain an isothiuronium salt of at least one kind selected from the group consisting of the isothiuronium salt having the skeleton of the polythiol compound (3), the isothiuronium salt having the skeleton of the polythiol compound (4), and the isothiuronium salt having the skeleton of the polythiol compound (5), and by initiating a rearrangement reaction, it is possible to obtain two or three among the abovementioned isothiuronium salts.

Reaction Scheme Example 3

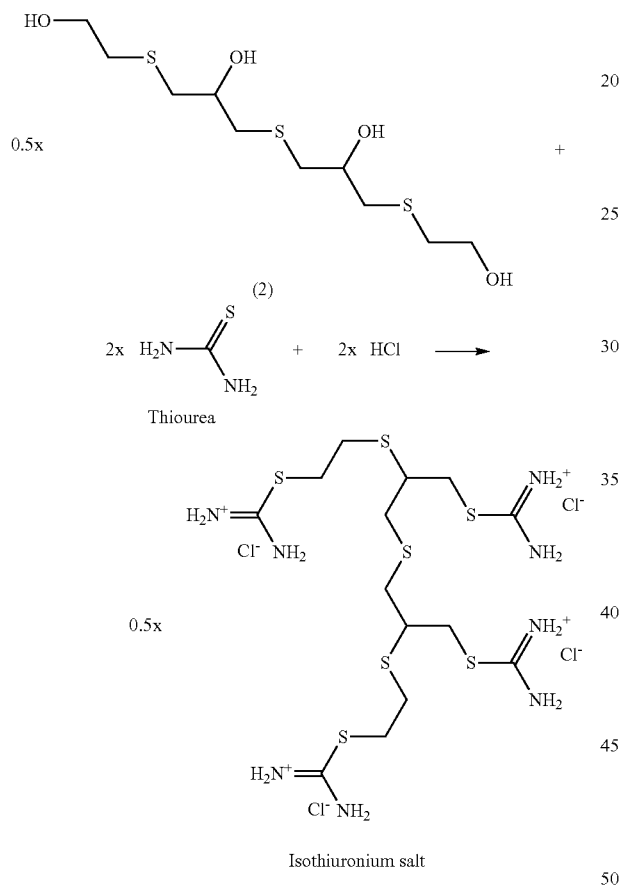

Isothiuronium salt

In the Reaction Scheme Example 3, an example is shown in which hydrogen chloride (HCl) is used as an acid, but the acid used in Step 3 is not limited to hydrogen chloride, and various inorganic acids and organic acids can be used. Examples of the inorganic acids include hydrogen chloride, sulfuric acid and the like, and examples of organic acids include formic acid and the like. The form of addition of an acid is not limited, and the acid can be added, for example, as an aqueous solution. The concentration of the acid in the aqueous solution is not particularly limited, and can be, for example, about 10% by mass to 80% by mass. In Step 3, the acid can be used at a ratio of, for example, 2.0 mol to 12.0 mol, or may be 3.0 mol to 8.0 mol, and thiourea can be used at a ratio of, for example, 3.0 mol to 6.0 mole, or 4.5 mol to 5.5 mol with respect to 1.0 mol of the polyol compound represented by Formula (2). The reaction temperature in Step 3 can be, for example, from 40° C. to the reflux temperature, or from about 90° C. to 120° C., and the reaction time can be, for example, about 1 h to 24 h.

(Step 4)

Step 4 is a step of hydrolyzing the isothiuronium salt obtained in Step 3 in the presence of a base to obtain a polythiol salt. The polythiol salt obtained herein has a structure in which a hydrogen atom of one or more thiol groups (—SH) among four thiol groups (—SH) present in one molecule in the structure of the polythiol compound represented by Formula (3), Formula (4) or Formula (5) is substituted. In Step 4, it is also possible to obtain two or more polythiol salts having different structures. The polythiol salt may be an alkali metal salt of polythiol or an ammonium salt of polythiol. The type of salt can be adjusted by the type of base used for hydrolysis. As an example, a mode of obtaining an alkali metal salt as a polythiol salt will be described hereinbelow.

The alkali metal salt of polythiol has a structure in which an alkali metal salt of a thiol group (—SM; M represents an alkali metal atom) is introduced in the molecular terminal as a result of hydrolysis of the isothiuronium salt obtained in Step 3. For example, by hydrolyzing the isothiuronium salt having the skeleton of the polythiol compound represented by Formula (3) by using sodium hydroxide as a base, it is possible to obtain the alkali metal salt (sodium salt) of the polythiol shown in the following Reaction Scheme Example 4.

Reaction Scheme Example 4

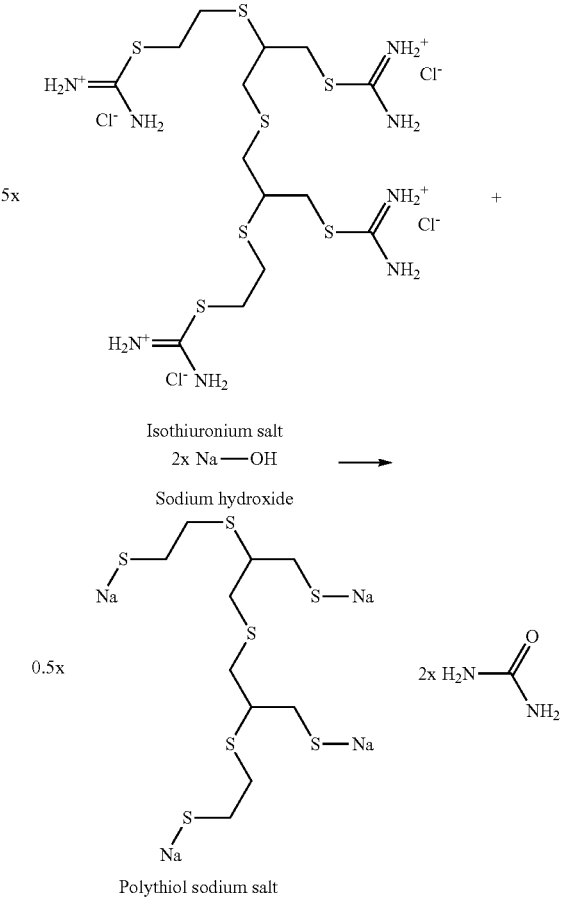

In the Reaction Scheme Example 4, an example is shown in which sodium hydroxide is used as the base. However, the base used in Step 4 is not limited to sodium hydroxide, and various inorganic bases and organic bases can be used. The base may be an inorganic base. Examples of the inorganic base include sodium hydroxide, potassium hydroxide, ammonia and the like. The form of base addition is not limited, but it is possible to add the base as an aqueous solution. By adding the base as an aqueous solution, it is possible to hydrolyze the isothiuronium salt with water contained in the aqueous solution in the presence of the base. The base concentration in the aqueous solution is not particularly limited, and can be, for example, about 10% by mass to 60% by mass. The base can be used at a ratio of, for example, 1.0 mol to 4.0 mol, 1.0 mol to 3.0 mol, or 1.2 mol to 2.0 mol with respect to 1.0 mol of the acid used in Step 3. An organic solvent can be added to the reaction solution including the isothiuronium salt after the reaction in Step 3. The organic solvent can be arbitrarily added at any stage after the reaction in Step 3. The amount of the organic solvent to be added can be, for example, about 0.2 times to 3.0 times, on the volume basis, that of the reaction solution after the reaction in Step 3. As the organic solvent, for example, toluene, xylene, benzene and the like can be mentioned. In Step 4, the reaction temperature can be, for example, about 10° C. to 80° C., and the reaction time can be, for example, about 1 h to 10 h.

(Step 5)

Step 5 is a step of converting the polythiol salt obtained in Step 4 into a polythiol with an acid. As a result, it is possible to obtain one or more polythiol compounds selected from the group consisting of the polythiol compound represented by Formula (3), the polythiol compound represented by Formula (4) and the polythiol compound represented by Formula (5). For example, Reaction Scheme Example 5 for converting the polythiol sodium salt shown in Reaction Scheme Example 4 to polythiol by using hydrogen chloride (HCl) as an acid to obtain the polythiol compound represented by Formula (3) is shown below.

Reaction Scheme Example 5

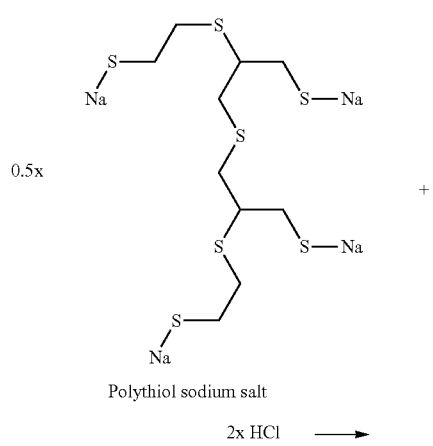

Polythiol sodium salt

2x HCl ⟶

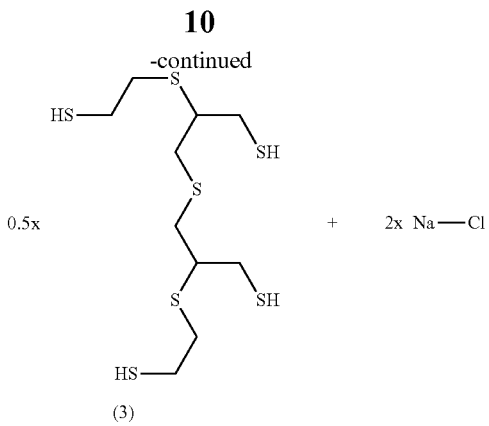

(3)

In the above Reaction Scheme Example 5, an example is shown in which hydrogen chloride is used as the acid. However, the acid to be used in Step 5 is not limited to hydrogen chloride, and various inorganic acids and organic acids can be used. The details relating to the acid to be used in Step 5 are as described in relation to the acid in Step 3. The conversion to polythiol with the acid in Step 5 can be carried out using the acid in the form of an aqueous solution, for example, by acid washing. It is possible to carry out water washing after acid washing, or to carry out acid washing two or more times and to wash with water between acid washing cycles. The temperature of the environment in which Step 5 is performed is not particularly limited. Step 5 can be performed in an environment with a temperature of, for example, of 10° C. to 60° C., or 20° C. to 45° C. When an organic solvent is used in any of the steps, a step of distilling off the organic solvent from the reaction solution after Step 5 may be carried out by a known method. Further, subsequent steps such as filtration and distillation can also be carried out by known methods.

Each of the above steps can be performed in the atmospheric air and also can be performed in an atmosphere other than the atmospheric air, for example, under a nitrogen atmosphere.

Through the above-described steps, it is possible to obtain a polythiol compound selected from the group consisting of a polythiol compound represented by the following Formula (3) (4,8-bismercaptomethyl-3,6,9-trithiaundecane-1,11-diol), a polythiol compound represented by the following Formula (4) (4,7-bismercaptomethyl-3,6,9-trithiaundecane-1,11-diol), and a polythiol compound represented by the following Formula (5) (5,7-bismercaptomethyl-3,6,9-trithiaundecane-1,11-diol) or a mixture of two or more of such polythiol compounds. When the polythiol compounds are obtained as a mixture of two or more thereof, each polythiol compound may be isolated by a known isolation method or the compounds may be used in the form of a mixture as a raw material for synthesizing various resins. With the method for producing a polythiol compound according to one aspect of the present disclosure, the polythiol compound can be advantageously obtained in a high yield.

Furthermore, according to one aspect of the present disclosure, a polythiol compound obtained by the above production method is also provided. The inventors of the present disclosure presume that increasing the refractive index of the polythiol compound is preferable from the viewpoint of improving the refractive index of the polythiourethane resin obtained by the curing reaction of the polythiol compound with a polyiso(thio)cyanate compound. Regarding this effect, the method for producing a polythiol compound according to one aspect of the present disclosure can also improve the refractive index of the polythiol compound in one aspect thereof.

Each of the polythiol compounds represented by Formula (3), (4), or (5) is a polyfunctional (tetrafunctional) polythiol compound having four thiol groups in a molecule. A cured product (polythiourethane resin) obtained by the curing reaction of such a polyfunctional polythiol compound with a polyiso(thio)cyanate compound can have various physical properties preferable for an optical component such as a spectacle lens.

[Method for Producing Curable Composition]

One aspect of the present disclosure relates to a method for producing a curable composition, including:

producing a polythiol compound by the method for producing a polythiol compound according to the abovementioned one aspect of the present disclosure; and preparing a curable composition by mixing the produced polythiol compound with a polyiso(thio)cyanate compound.

Furthermore, according to still another aspect of the present disclosure, a curable composition that is obtained by the production method is also provided.

By curing the curable composition obtained by the production method, a polythiourethane resin useful as a material for an optical component such as a spectacle lens can be obtained as a cured product.

Hereinafter, the production method of the curable composition will be described in greater detail.

Details of the step of producing a polythiol compound are as described above in relation to the method for producing a polythiol compound according to one aspect of the present disclosure. A curable composition can be prepared by mixing the thus produced polythiol compound with a polyiso(thio)cyanate compound. In the present disclosure and in the present description, the term "polyiso(thio)cyanate compound" is intended to be inclusive of a polyisocyanate compound and a polyisothiocyanate compound. Incidentally, isocyanate can be represented by "isocyanato", and isothiocyanate can be represented by "isothiocyanato". In addition, the term "iso(thio)cyanate group" is intended to be inclusive of an isocyanate group (—N=C=O) and an isothiocyanate group (—N=C=S). A "polyiso(thio)cyanate compound" is a polyfunctional compound having two or more iso(thio)cyanate groups in a molecule. As a result of reactive curing of a polythiol compound with a polyiso(thio)cyanate compound, the thiol group of the polythiol compound reacts with the iso(thio)cyanate group of the polyiso(thio)cyanate compound, and a reaction product having the following bond:

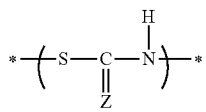

in a molecule can be obtained. In this formula, Z is an oxygen atom or a sulfur atom. As a result of reacting the thiol group with the isocyanate group, X forms the above-mentioned bond with the oxygen atom, and as a result of reacting with the isothiocyanate group, X forms the above-mentioned bond with the sulfur atom. In the present disclosure and the present description, a reaction product (resin) having a plurality of the abovementioned bonds in a molecule is described as "polythiourethane resin".

As the polyiso(thio)cyanate compound, various polyiso(thio)cyanate compounds such as aliphatic polyiso(thio)cyanate compounds, alicyclic polyiso(thio)cyanate compounds and aromatic polyiso(thio)cyanate compounds can be used. The number of iso(thio)cyanate groups contained in one molecule of the polyiso(thio)cyanate compound is 2 or more, may be 2 to 4, or may be 2 or 3. Specific examples of polyiso(thio)cyanate compounds include various compounds exemplified as polyiso(thio)cyanate compounds, for example, in paragraph 0052 of Japanese Patent No. 5319037 (the entire disclosure of which is hereby specifically incorporated by reference). Examples of polyiso(thio)cyanate compounds include aliphatic polyisocyanate compounds such as hexamethylene diisocyanate, 1,5-pentane diisocyanate, isophorone diisocyanate, bis(isocyanatomethyl)cyclohexane, dicyclohexylmethane diisocyanate, 2,5-bis(isocyanatomethyl)-bicyclo[2.2.1]heptane, 2,6-bis(isocyanatomethyl)-bicyclo[2.2.1]heptane, bis(4-isocyanatocyclohexyl)methane, 1,3-bis(isocyanatomethyl)cyclohexane and 1,4-bis(isocyanatomethyl)cyclohexane, and aromatic polyisocyanate compounds such as xylylene diisocyanate, 1,3-diisocyanatobenzene, tolylene diisocyanate, 2,4-diisocyanatotoluene, 2,6-disocyanatotoluene and 4,4'-methylenebis(phenylisocyanate). Further, halogen substituents such as chlorine substituents and bromine substituents, alkyl substituents, alkoxy substituents, nitro substituents, prepolymer modification products with polyhydric alcohols, carbodiimide modification products, urea modification products, biuret modification products, dimer modification products, and trimer modification products of the polyiso(thio)cyanate compound can be also used. These compounds may be used singly or in combination of two or more thereof.

The curable composition can be prepared by mixing the polythiol compound with a polyiso(thio)cyanate compound. The mixing ratio of the polythiol compound and the polyiso(thio)cyanate compound in the curable composition is not particularly limited and can be, for example, in the range of 0.5 to 3.0, in the range of 0.6 to 2.0, or in the range of 0.8 to 1.3, as a molar ratio of thiol groups contained in the polythiol compound to iso(thio)cyanate groups contained in the polyiso(thio)cyanate compound. Setting the mixing ratio within the above ranges is possible in terms of obtaining a curable composition capable of providing a cured product having various excellent physical properties such as high refractive index and high heat resistance. Further, in one aspect, the curable composition can include, for example, 40% by mass or more (for example, 40% by mass to 70% by mass) of the polythiol compound with respect to 100% by mass of the total amount of the curable composition.

At the time of preparing the curable composition, one or more components other than the polythiol compound and the polyiso(thio)cyanate compound may be mixed. Specific examples of such other components include, for example, a reaction catalyst for the curing reaction between the polythiol compound and the polyiso(thio)cyanate compound. For other components that may be mixed, see, for example, Japanese Patent No. 5319037, paragraphs 0055, 0057, and 0058 to 0064. In addition, it is also possible to use one or more additives commercially available as additives for various resins such as polythiourethane resins. The curable composition can be prepared by mixing the above-described various components at the same time or sequentially in any order. The preparation method is not particularly limited, and any known method for preparing curable compositions can be used without any limitation.

[Method for Producing Cured Product]

According to one aspect of the present disclosure, there is provided a method for producing a cured product, including:

producing a curable composition by the production method according to the abovementioned one aspect of the present disclosure; and curing the produced curable composition to obtain a cured product.

According to yet another aspect of the present disclosure, there is also provided a cured product obtained by the abovementioned production method.

Hereinafter, the method for producing a cured product will be described in greater detail.

Details relating to the step of producing the curable composition are as described above in relation to the method for producing the curable composition according to one aspect of the present disclosure. By curing the curable composition thus produced, it is possible to obtain a polythiourethane resin useful as a material for an optical component such as a spectacle lens as a cured product. The results of intensive investigation performed by the inventors of the present disclosure made it clear that by using the polythiol compound obtained by the method for producing a polythiol compound according to one aspect of the present disclosure as a raw material for synthesis, it is possible to improve the refractive index of the obtained polythiourethane resin. Regarding the improvement of the refractive index, from the viewpoint of reducing the thickness of an optical component such as a spectacle lens, it is important that the refractive index ne measured in the below-described Examples be improved by 0.002 or more. Further, in one aspect, by using the polythiol compound obtained by the method for producing a polythiol compound according to one aspect of the present disclosure as a raw material for synthesis, it is also possible to improve heat resistance of the obtained polythiourethane resin. During processing of optical components such as spectacle lenses, in many cases, heat treatment is carried out in the step of forming a functional film or the like, and it is therefore desirable that a polythiourethane resin used as the base material of the optical component have heat resistance capable of withstanding such heat treatment. An indicator of heat resistance can be exemplified by a glass transition temperature (Tg). The glass transition temperature (Tg) in the present disclosure and the present description refers to a glass transition temperature measured by thermomechanical analysis (TMA) penetration method according to JIS K7196-2012. For a specific measurement method, refer to the below-described Examples. Regarding the heat resistance with the glass transition temperature (Tg) as an index, it is possible that the increase in heat resistance be 2° C. or more as Tg.

The curing reaction between the polythiol compound and the polyiso(thio)cyanate compound can be carried out by various types of curing treatment capable of curing the curable composition. For example, cast polymerization is possible for producing a cured product having a lens shape (also referred to as "plastic lens"). In cast polymerization, a cured product can be obtained by injecting a curable composition into a cavity of a molding die having two opposed molds with a predetermined gap therebetween and a cavity formed by closing the gap, and polymerizing (curing) the curable composition inside the cavity. For details of molds that can be used for cast polymerization, see paragraphs 0012 to 0014 of Japanese Patent Application Laid-open No. 2009-262480 (the entire disclosure of which is hereby specifically incorporated by reference) and FIG. 1 of the same publication. In this publication, a molding die in which the gap between the two molds is closed with a gasket as a sealing member is shown, but a tape can also be used as the sealing member.

In one aspect, cast polymerization can be carried out in the following manner. The curable composition is poured into a molding die cavity from an injection port provided on the side of the molding die. After the injection, the curable composition may be polymerized (curing reaction) by heating, whereby the curable composition is cured to obtain a cured product onto which the inner shape of the cavity has been transferred. The polymerization conditions are not particularly limited, and can be appropriately set according to the composition of the curable composition or the like. As an example, the molding die with the curable composition injected into the cavity can be heated at a heating temperature of 20° C. to 150° C. for about 1 h to 72 h, but this condition is not limiting. In the present disclosure and the present description, the temperature such as the heating temperature and the like relating to cast polymerization is the temperature of the atmosphere in which the molding die is disposed. In addition, it is possible to raise the temperature at an arbitrary heating rate during heating, and to lower the temperature (cool down) at an arbitrary temperature lowering rate. After completion of the polymerization (curing reaction), the cured product inside the cavity is released from the molding die. The cured product can be released from the molding die by removing the upper and lower molds forming the cavity and the gasket or tape in an arbitrary order, as is usually done in cast polymerization. The cured product released from the mold can be used as a lens base material for spectacle lenses. The cured product to be used as the lens base material for spectacle lenses usually can be subjected to post-processing after the release from the molding die, for example, annealing, a grinding step such as a rounding step, a polishing step, and a coat layer forming step of forming a primer coat layer for improving impact resistance, a hard coat layer for improving the surface hardness, and the like. Further, various functional layers such as an antireflection layer and a water-repellent layer can be formed on the lens base material. For any of these steps, known techniques can be used without any limitation. Thus, a spectacle lens in which the lens base material is the cured product can be obtained. Further, by attaching this spectacle lens to the frame, glasses can be obtained.

EXAMPLES

Next, the present disclosure will be described in greater detail with reference to Examples, but the present disclosure is not limited to the aspects shown in the Examples. Operations and evaluations described below were carried out in air at room temperature (about 20° C. to 25° C.) unless otherwise specified. In addition, "%" and "parts" described below are based on mass unless otherwise specified.

Example 1

<Production of Polythiol Compound>

(Step 1)

A total of 96.2 g (1.04 mol) of epichlorohydrin was dropwise added over 1 h to a mixed solution of 78.1 g (1.00 mol) of 2-mercaptoethanol and 2.0 g of triethylamine while keeping the internal temperature at 35° C. to 40° C., and the mixture was aged for 1 h at an internal temperature of 40° C. The aging here and the aging described below were carried out while stirring the reaction solution.

(Step 2)

An aqueous solution prepared by dissolving 124.9 g (0.52 mol) of sodium sulfide nonahydrate in 100 g of pure water was added dropwise over 1 h to the reaction solution after the aging while keeping the internal temperature at 40° C. to 45° C., followed by aging for 1 h at 45° C.

(Step 3)

Next, 303.8 g (3.00 mol) of 36% hydrochloric acid and 190.3 g (2.50 mol) of thiourea were added to the reaction solution, followed by heating and stirring for 9 h at an internal temperature of 110° C.

(Step 4)

After cooling the reaction solution to room temperature, 400 ml of toluene was added, 600.4 g (4.50 mol) of a 30% sodium hydroxide aqueous solution was gradually added and hydrolysis was carried for 4 h out at an internal temperature of 60° C.

(Step 5)

The reaction solution after the hydrolysis was allowed to stand to separate the solution into an aqueous layer and an organic layer, the organic layer was then taken out, and the organic layer was successively washed twice with 100 ml of 36% hydrochloric acid and 100 ml of water. Toluene in the organic layer after washing was distilled off with a rotary evaporator to obtain a polythiol compound in a yield of 174.4 g (yield ratio 95.1%).

In Example 1, in Step 3, the rearrangement reaction occurs as described above, whereby a mixture of the isothiuronium salt having the skeleton of the polythiol compound represented by Formula (3), the isothiuronium salt having the skeleton of the polythiol compound represented by Formula (4), and the isothiuronium salt having the skeleton of the polythiol compound represented by Formula (5) can be obtained. As a result, in Step 5, a mixture of the polythiol compound represented by Formula (3), the polythiol compound represented by Formula (4), and the polythiol compound represented by Formula (5) is obtained. The yield ratio was calculated by the formula Yield Ratio=[(the abovementioned yield)/(theoretical yield)]×100 by using the theoretical yield determined from the theoretical molar yield (0.50 mol) of the polythiol compounds represented by Formulas (3) to (5) obtained from the amount of 2-mercaptoethanol (1.00 mol) used in Step 1.

Mixtures of the polythiol compound represented by Formula (3), the polythiol compound represented by Formula (4), and the polythiol compound represented by Formula (5) are similarly obtained in the Examples and Comparative Examples described hereinbelow. In the below-described Examples and Comparative Examples, the yield ratio was calculated in a similar manner.

The polythiol compounds obtained in the Examples and Comparative Examples were used as they were, without treatment such as purification, for the production of the following cured products and the evaluation of polythiol compounds.

<Production of Cured Product (Plastic Lens) A>

A total of 50.60 parts of xylylene diisocyanate, 0.01 parts of dimethyltin dichloride as a curing catalyst, 0.20 parts of an acidic phosphoric acid ester (JP-506H, manufactured by Johoku Chemical Co., Ltd.) as a releasing agent, and 0.50 parts of an ultraviolet absorber (SEESORB 701, manufactured by Shipro Kasei Kaisha, Ltd.) were mixed and dissolved.

Further, 49.40 parts of the polythiol compound obtained above was added and mixed to obtain a mixed solution. This mixed solution was deaerated for 1 h at 200 Pa, and then filtration was carried out with a PTFE (polytetrafluoroethylene) filter having a pore size of 5.0 μm. The filtered mixed solution (curable composition) was injected into a molding die for a lens made of a glass mold having a diameter of 75 mm and −4.00 D and a tape. The molding die was loaded into an electric furnace, gradually heated over 20 h from 15° C. to 120° C., and kept for 2 h for polymerization (curing reaction). After completion of the polymerization, the molding die was removed from the electric furnace and the polymer was released to obtain a cured product (plastic lens). The resulting plastic lens was further annealed for 3 h in an annealing furnace having a furnace temperature of 120° C.

<Production of Cured Product (Plastic Lens) B>

A total of 58.90 parts of dicyclohexylmethane diisocyanate, 0.3 parts of dimethyltin dichloride as a curing catalyst, 0.20 parts of an acidic phosphoric acid ester (JP-506H manufactured by Johoku Chemical Co., Ltd.) as a releasing agent, and 1.00 part of an ultraviolet absorber (SEESORB 701, manufactured by Shipro Kasei Kaisha, Ltd.) were mixed and dissolved.

Further, 41.10 parts of the polythiol compound obtained by the production of the polythiol compound was added and mixed to obtain a mixed solution. This mixed solution was deaerated for 1 h at 200 Pa, and then filtration was carried out with a PTFE (polytetrafluoroethylene) filter having a pore size of 5.0 μm. The filtered mixed solution (curable composition) was injected into a molding die for a lens made of a glass mold having a diameter of 75 mm and −4.00 D and a tape. The molding die was loaded into an electric furnace, gradually heated over 20 h from 15° C. to 120° C., and kept for 2 h for polymerization (curing reaction). After completion of the polymerization, the molding die was removed from the electric furnace and the polymer was released to obtain a cured product (plastic lens). The resulting plastic lens was further annealed for 3 h in an annealing furnace having a furnace temperature of 120° C.

Examples 2 to 4, Comparative Examples 1 to 5

Polythiol compounds were obtained by the same method as in Example 1 except that the charged amount of epichlorohydrin in Step 1 and the charged amount of sodium sulfide nonahydrate in Step 2 were changed. The equivalents of epichlorohydrin used in Step 1 and sodium sulfide (sodium sulfide nonahydrate) used in Step 2 with respect to 2-mercaptomethanol used in Step 1 are shown in Table 1.

A cured product A and a cured product B were produced in the same manner as in Example 1 by using the obtained polythiol compound.

[Evaluation Methods]

<Refractive Index of Cured Product (Plastic Lens)>

The refractive index ne of the cured product (plastic lens) produced above was measured by the following method by using a precision refractive index meter KPR-200 manufactured by Shimadzu Corporation.

(1) Using a precision cutting machine Isomet manufactured by Buehler, a test sample in the form of a triangular prism having an angle of 90° between two surfaces in contact with the measuring prism is prepared.

(2) The prepared sample is set in the measuring prism and the refractive index ne is measured under the following measurement conditions.

(Measurement Conditions)

Measurement temperature: 25° C.

Contact liquid: bromonaphthalene

<Glass Transition Temperature of Cured Product (Plastic Lens)>

The glass transition temperature (Tg) of the cured product (plastic lens) produced in the above-described manner was measured by a penetration method using a thermal instrument analyzer TMA 8310 manufactured by Rigaku Corporation. The load at the time of measurement was 10 g, the heating rate was 10 K/min, and an indenter with a diameter of 0.5 mm was used as an indenter for the penetration method.

<Refractive Index of Polythiol Compound>

The refractive index ne of the polythiol compound prepared in the above-described manner was measured using a refractometer RA-500 manufactured by Kyoto Electronics Manufacturing Co., Ltd.

<Thiol Equivalent of Polythiol Compound>

The thiol equivalents of the polythiol compounds obtained in the respective Examples and Comparative Examples were measured by the following method by using an automatic titration device AT-610 manufactured by Kyoto Electronics Manufacturing Co., Ltd.

(1) A total of 0.1 g of the polythiol compound obtained in each Example and Comparative Example are accurately weighed.

(2) The accurately weighed polythiol compound is dissolved in a mixed solvent of 40 ml of chloroform and 20 ml of 2-propanol to prepare a sample for measurement.

(3) Titration of the prepared measurement sample is carried out using a titration solution (0.05 mol/L iodine solution), and an end point is determined.

(4) The thiol equivalent is determined from the titration amount (mL) at the end point by the following formula.

Thiol equivalent=[(Sample amount (g))×(Titration solution factor)×10000]/Titer (mL)

The above results are shown in Table 1. From the results shown in Table 1, it can be confirmed that the refractive index of the cured product in Examples is improved (improvement of the refractive index ne by 0.02 or more) compared with Comparative Examples.

Further, it can be confirmed that in Examples, the yield ratio and the refractive index of the polythiol compound and the heat resistance of the cured product are all improved compared with Comparative Examples.

The inventors of the present disclosure believe that the thiol equivalent shown in Table 1 is a value that can be used as an index of the purity of the target product in the produced polythiol compound. Details are explained hereinbelow.

The theoretical value of the equivalent for a functional group (for example, a thiol group) of a certain compound can be obtained by dividing the molecular weight of the compound by the number of functional groups contained in one molecule. The polythiol compound represented by Formula (3), the polythiol compound represented by Formula (4), and the polythiol compound represented by Formula (5) are each a tetrafunctional polythiol compound having four thiol groups, and the theoretical value of the equivalent (thiol equivalent) for the thiol group is 92. Meanwhile, as the amount of by-products of trifunctional or less functional thiol compounds other than the above-mentioned three tetrafunctional polythiol compounds, which are the target products in the production of the polythiol compound, increases, the actually measured value of the thiol equivalent greatly exceeds 92. Therefore, the inventors of the present disclosure believe that the thiol equivalent can be used as an index of the purity of the three polythiol compounds which are the target products in the polythiol compounds produced in respective Examples and Comparative Examples. As shown in Table 1, the thiol equivalents of the polythiol compounds prepared in Examples 1 to 4 are closer to the theoretical value 92 than those of the polythiol compounds produced in Comparative Examples 1 to 5. The inventors of the present disclosure presume that the fact that above-mentioned three polythiol compounds, which are the target products, are obtained at high purity is a factor contributing to the improvement of the refractive index of the cured product. In consideration of this point, in one aspect, the measured value of the thiol equivalent of the polythiol compound obtained by the method for producing a polythiol compound according to one aspect of the present disclosure is for example, 92 or more and 100 or less.

However, the above presumption of the inventors of the present disclosure places no limitation on the present disclosure.

TABLE 1

| | Equivalent | | Polythiol compound | | | Cured product A | | Cured product B | |
| --- | --- | --- | --- | --- | --- | --- | --- | --- | --- |
| | Epichlorohydrin | Sodium sulfide | Refractive index | Thiol equivalent | Yield ratio | Refractive index | Heat resistance, glass transition temperature (° C.) | Refractive index | Heat resistance, glass transition temperature (° C.) |
| Example 1 | 1.04 | 1.04 | 1.6455 | 97 | 95.1% | 1.669 | 103 | 1.602 | 142 |
| Example 2 | 1.00 | 1.04 | 1.6457 | 98 | 93.4% | 1.669 | 104 | 1.602 | 141 |
| Example 3 | 1.00 | 1.20 | 1.6452 | 99 | 93.6% | 1.669 | 103 | 1.602 | 142 |
| Example 4 | 1.25 | 1.25 | 1.6450 | 99 | 91.4% | 1.668 | 102 | 1.601 | 141 |
| Comparative Example 1 | 1.00 | 1.00 | 1.6430 | 103 | 87.6% | 1.666 | 99 | 1.600 | 139 |
| Comparative Example 2 | 1.30 | 1.30 | 1.6426 | 103 | 85.3% | 1.663 | 97 | 1.598 | 136 |
| Comparative Example 3 | 0.96 | 1.10 | 1.6427 | 104 | 82.2% | 1.662 | 96 | 1.597 | 137 |
| Comparative Example 4 | 1.00 | 1.34 | 1.6426 | 103 | 84.5% | 1.663 | 97 | 1.598 | 138 |
| Comparative Example 5 | 1.28 | 1.04 | 1.6428 | 103 | 83.2% | 1.663 | 98 | 1.597 | 137 |

Finally, the above-mentioned aspects are summarized.

According to one aspect, there is provided a method for producing a polythiol compound, including: Step 1 of reacting 2-mercaptoethanol with an epihalohydrin in an amount of 1.00 equivalent or more and 1.25 equivalent or less with respect to the 2-mercaptoethanol to obtain a polyol compound represented by Formula (1); Step 2 of reacting the polyol compound represented by Formula (1) with an alkali metal sulfide in an amount of 1.04 equivalent or more and 1.25 equivalent or less with respect to the 2-mercaptoethanol to obtain a polyol compound represented by Formula (2); Step 3 of reacting the polyol compound represented by Formula (2) with thiourea in the presence of an acid to obtain an isothiuronium salt; Step 4 of hydrolyzing the isothiuronium salt in the presence of a base to obtain a polythiol salt; and Step 5 of converting the polythiol salt into a polythiol with an acid to obtain one or more polythiol compounds selected from the group consisting of a polythiol compound represented by Formula (3), a polythiol compound represented by Formula (4), and a polythiol compound represented by Formula (5).

By subjecting the polythiol compound obtained by the above-mentioned method for producing a polythiol compound to the curing reaction with a polyiso(thio)cyanate compound, it is possible to provide a cured product (polythiourethane resin) having a high refractive index.

In one aspect, the equivalent of epihalohydrin in Step 1 may be 1.20 equivalent or less, may be 1.15 equivalent or less, may be 1.10 equivalent or less, or may be 1.05 equivalent or less with respect to the 2-mercaptoethanol.

In one aspect, the equivalent of the alkali metal sulfide in Step 2 may be 1.20 equivalent or less, may be 1.15 equivalents or less, or may be 1.10 equivalent or less with respect to the 2-mercaptoethanol used in Step 1.

According to further aspect, there is provided a method for producing a curable composition, including: producing a polythiol compound by the abovementioned production method; and mixing the produced polythiol compound with a polyiso(thio)cyanate compound to prepare a curable composition.

According to still further aspect, there is provided a method for producing a cured product, including: producing a curable composition by the abovementioned production method; and curing the produced curable composition to obtain a cured product.

In one aspect, the curing is carried out by subjecting the curable composition to cast polymerization.

In one aspect, the cured product is a spectacle lens base material.

Two or more of the various aspects disclosed in this description can be combined in any combination.

It should be taken into account that the embodiments disclosed herein are exemplary in all respects and are not restrictive. The scope of the present disclosure is defined not by the description above but by the claims, and is intended to include all modifications within the meaning and scope equivalent to the claims.

One aspect of the present disclosure is useful in the field of manufacturing various kinds of optical components such as spectacle lenses.

What is claimed is:

1. A method for producing a polythiol compound, comprising:
    reacting 2-mercaptoethanol with an epihalohydrin in an amount of 1.00 equivalent or more and 1.25 equivalent or less with respect to the 2-mercaptoethanol to obtain a polyol compound represented by Formula (1);

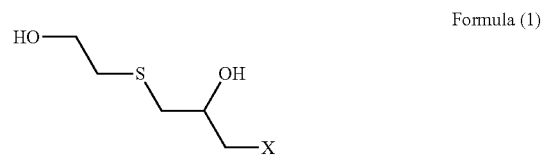

Formula (1)

[in Formula (1), X represents a halogen atom]

reacting the polyol compound represented by Formula (1) with an alkali metal sulfide in an amount of 1.04 equivalent or more and 1.25 equivalent or less with respect to the 2-mercaptoethanol to obtain a polyol compound represented by Formula (2);

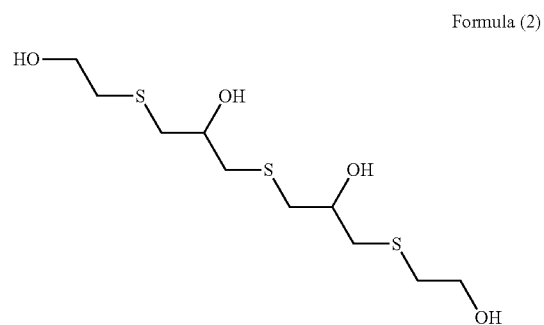 [SMILES: OCCSCC(O)CSCC(O)CSCCO]

Formula (2)

reacting the polyol compound represented by Formula (2) with thiourea in the presence of an acid to obtain an isothiuronium salt;

hydrolyzing the isothiuronium salt in the presence of a base to obtain a polythiol salt; and converting the polythiol salt into a polythiol with an acid to obtain one or more polythiol compounds selected from the group consisting of a polythiol compound represented by Formula (3), a polythiol compound represented by Formula (4), and a polythiol compound represented by Formula (5)

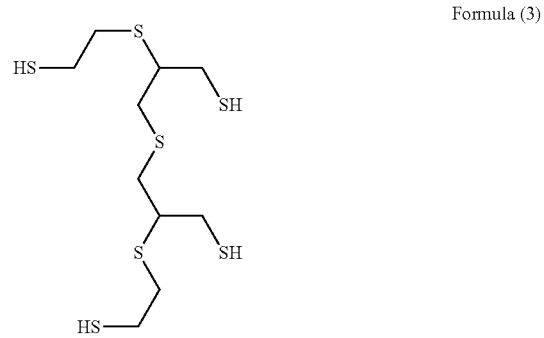

Formula (3)

-continued

Formula (4)

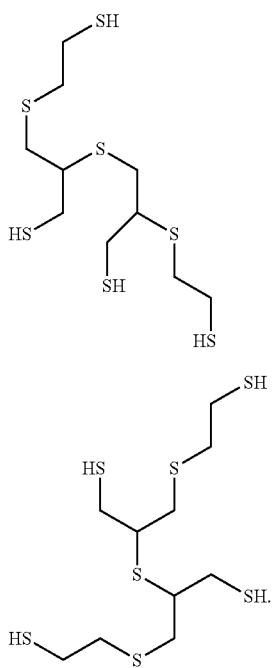

Formula (5)

2. A method for producing a curable composition, comprising:
   producing a polythiol compound by the production method according to claim 1; and
   mixing the produced polythiol compound with a polyiso(thio)cyanate compound to prepare a curable composition.

3. A method for producing a cured product, comprising:
   producing a curable composition by the production method according to claim 2; and
   curing the produced curable composition to obtain a cured product.

4. The method for producing a cured product according to claim 3, wherein
   the curing is carried out by subjecting the curable composition to cast polymerization.

5. The method for producing a cured product according to claim 3, wherein
   the cured product is a spectacle lens base material.

6. The method for producing a cured product according to claim 4, wherein
   the cured product is a spectacle lens base material.

* * * * *